United States Patent
Fadler et al.

(10) Patent No.: US 8,025,441 B2
(45) Date of Patent: Sep. 27, 2011

(54) MOVEMENT SYSTEM FOR AN X-RAY C-ARM

(75) Inventors: Franz Fadler, Hetzles (DE); Norbert Herrmann, Ebnath (DE); Manfred Sechser, Neusorg (DE)

(73) Assignee: Siemens Aktiengesellschaft, Munich (DE)

( * ) Notice: Subject to any disclaimer, the term of this patent is extended or adjusted under 35 U.S.C. 154(b) by 163 days.

(21) Appl. No.: 12/490,970

(22) Filed: Jun. 24, 2009

(65) Prior Publication Data

US 2010/0027761 A1   Feb. 4, 2010

(30) Foreign Application Priority Data

Jun. 30, 2008 (DE) .......................... 10 2008 030 839

(51) Int. Cl.
*H05G 1/02* (2006.01)

(52) U.S. Cl. ........................................ 378/197; 378/196

(58) Field of Classification Search .................. 378/197, 378/196, 198
See application file for complete search history.

(56) References Cited

U.S. PATENT DOCUMENTS

| 4,433,951 A * | 2/1984 | Koch et al. ................. 414/217 |
| 6,609,826 B1 | 8/2003 | Fujii et al. |
| 7,534,036 B2 * | 5/2009 | Delmas et al. ................. 378/196 |
| 2006/0120511 A1 | 6/2006 | Gregerson et al. |
| 2009/0185662 A1 * | 7/2009 | Gross et al. ................... 378/197 |

FOREIGN PATENT DOCUMENTS

DE  10 2005 048 391 B3   4/2007

OTHER PUBLICATIONS

German Office Action dated Mar. 5, 2009 with English translation.

* cited by examiner

*Primary Examiner* — Hoon Song
(74) *Attorney, Agent, or Firm* — Lempia Summerfield Katz LLC

(57) ABSTRACT

A movement system for a C-arm. The movement system comprises at least one first guide element arranged in a plane, a movement device arranged to allow movement along the first guide element as well as a first motion link rotatable around a first axis of rotation standing at right angles to the plane. The movement device is connected rotatably to the first motion link to a second axis of rotation standing at right angles to the plane such that a movement of the movement device along the first guide element causes the second axis of rotation to be moved on a circular track around the first axis of rotation. The advantage of this is that the arm is prevented from jamming as a result of leverages during movement of a C-arm.

10 Claims, 5 Drawing Sheets

MOVEMENT SYSTEM FOR AN X-RAY C-ARM

This patent document claims the benefit of DE 10 2008 030 839.0 filed Jun. 30, 2008, which is hereby incorporated by reference.

BACKGROUND

Mobile x-ray systems, which have C-arms, are used in surgical interventions in the operating room. As a result of the high degree of mobility, the mobile x-ray systems can be easily moved by the medical personnel away from the patient supported on the operating table (patient bed) and back towards the medical personnel again during the intervention. Over the course of rationalizations and when used in small operating rooms, it is advantageous for the relatively heavy C-arm system not to have to be moved too frequently in its entirety. Preferably, only the C-arm with x-ray emitter and x-ray detector is moved within specific limits but not the entire mobile x-ray system. Positions to which the arm has already been moved can be reached once more automatically and precisely.

U.S. Pat. No. 6,609,826 B1 describes how a C-arm can be moved horizontally and in parallel to a patient bed. U.S. Pat. No. 6,609,826 B1 claims a movement facility between a C-arm and a retaining facility, with the C-arm being able to be moved in a horizontal direction at right angles to an arm. The C-arm, however, can jam because of the parallel linear guides employed and the weight of the C-arm. An unfavorable lever relationship between an introduction of the movement force and the distance to the linear guides may cause the C-arm to jam.

DE 10 2005 048 391 B3 specifies a stand for a radiation therapy device. The stand includes an adjustable-length longitudinal support arm, an arm supported in the support arm rotatable around a first axis at right angles to the support arm, and a flat detector element rotatable in the arm around a second axis in parallel to the first axis, which is essentially aligned in parallel to the support arm. When the arm is rotated, the parallel alignment of the detector element to the support arm is retained, and with a motor for driving the rotation of the arm. The rotation of the arm is driven by a first gear connected to the motor and the rotation of the detector element by a gear operating in the reverse direction to the first gear connected to the same motor. The layout with a single motor and two gears operating in opposite directions makes precise positioning possible and simultaneously requires little installation volume or space.

US 2006/0120511 discloses a method and a facility for positioning a gantry of an x-ray imaging device in relation to an object to be examined are described. The method and facility make up to 5 degrees of freedom of movement possible.

SUMMARY AND DESCRIPTION

The present embodiments may obviate one or more of the drawbacks or limitations inherent in the related art. For example, in one embodiment, an improved movement facility allows a parallel movement of an x-ray C-arm to a patient bed.

In one embodiment, a movement system for a C-arm arranged on a trolley is provided. The movement system includes at least one first guide element arranged in one plane, a movement device arranged to allow movement along the first guide element, and a first motion link able to be rotated around an axis of rotation standing at right angles to the plane. The movement device is rotatably connected to the first motion link at a second axis of rotation standing at right angles to the plane, such that a movement of the movement facility along the first guide element causes the second axis of rotation to be moved on a circular track around the first axis of rotation. The movement system may include a second motion link establishing the rotatable connection between the movement device and the first motion link and at least one second guide element arranged on the second motion link in parallel to the plane and at right angles to the first guide element. The movement device is able to be moved along the second guide element. Accordingly, jamming, as a result of leverages during the movement of C-arm, is prevented, unlike in linear guides running in parallel. Length compensation at right angles to the direction of movement may be guaranteed during movement.

In another embodiment, the plane can be aligned horizontally. Accordingly, a C-arm may be moved parallel to an operator interface or to a patient bed.

First and second motion links may form a double motion link. The second motion link may be arranged above the first motion link. The double motion link provides a secure transmission of force. A drive device actively connected to the movement device can be designed and arranged on the second motion link such that, on movement of the movement device along the second guide means, the movement device is moved along the first guide. The drive device may be an electric motor drive.

A leverage acting on the movement device can be introduced partly via the first motion link into the first axis of rotation. This makes an optimum non-jamming distribution of force possible.

The movement device may include a first carriage movable in or on the first guide element and a second carriage movable in or on the second guide element. The first guide element may include a first rail system and the second guide element may include a second rail system. Accordingly, the implementation may have a low cost.

The movement device may be moved approximately +/−200 mm around a central position. This allows a C-arm to be moved sufficiently along a patient bed.

In one embodiment, a C-arm may include the movement system. The C-arm may be arranged on the movement device such that the C-arm can be moved in parallel to a patient bed. The C-arm may be easily and automatically used repositionably even in an operating room.

An x-ray facility may include a C-arm with the movement system.

Further special features and advantages are evident from the explanations of an exemplary embodiments given below which refer to schematic drawings.

DETAILED DESCRIPTION

Figure 1:
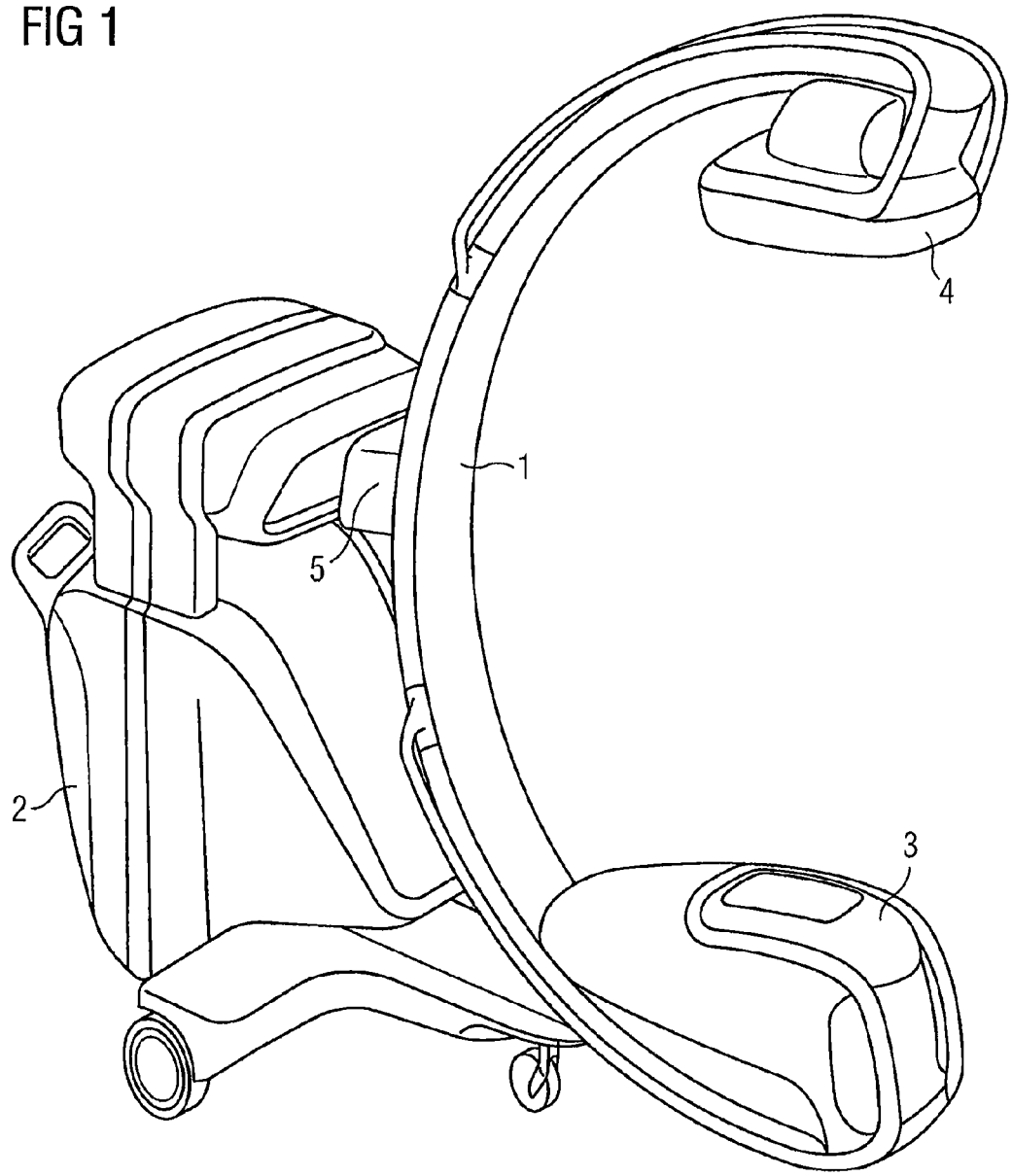
FIG. 1 illustrates one embodiment of a mobile C-arm x-ray device.

FIG. 1 shows one embodiment of a mobile C-arm x-ray system. The mobile C-arm x-ray system includes a mobile C-arm x-ray 1 arranged on a trolley with rollers. The C-arm x-ray device 1 and the trolley 2 are connected to each other via a C-arm support module 5. The ends of the x-ray C-arm have an x-ray emitter 3 or an x-ray detector 4, respectively. The x-ray emitter 3, for example, may irradiate a patient located on a bed with x-rays, which are captured by an x-ray detector 4. The x-ray C-arm 1 connected to the C-arm support module 5 is able to be moved horizontally by a movement system.

Figure 2:
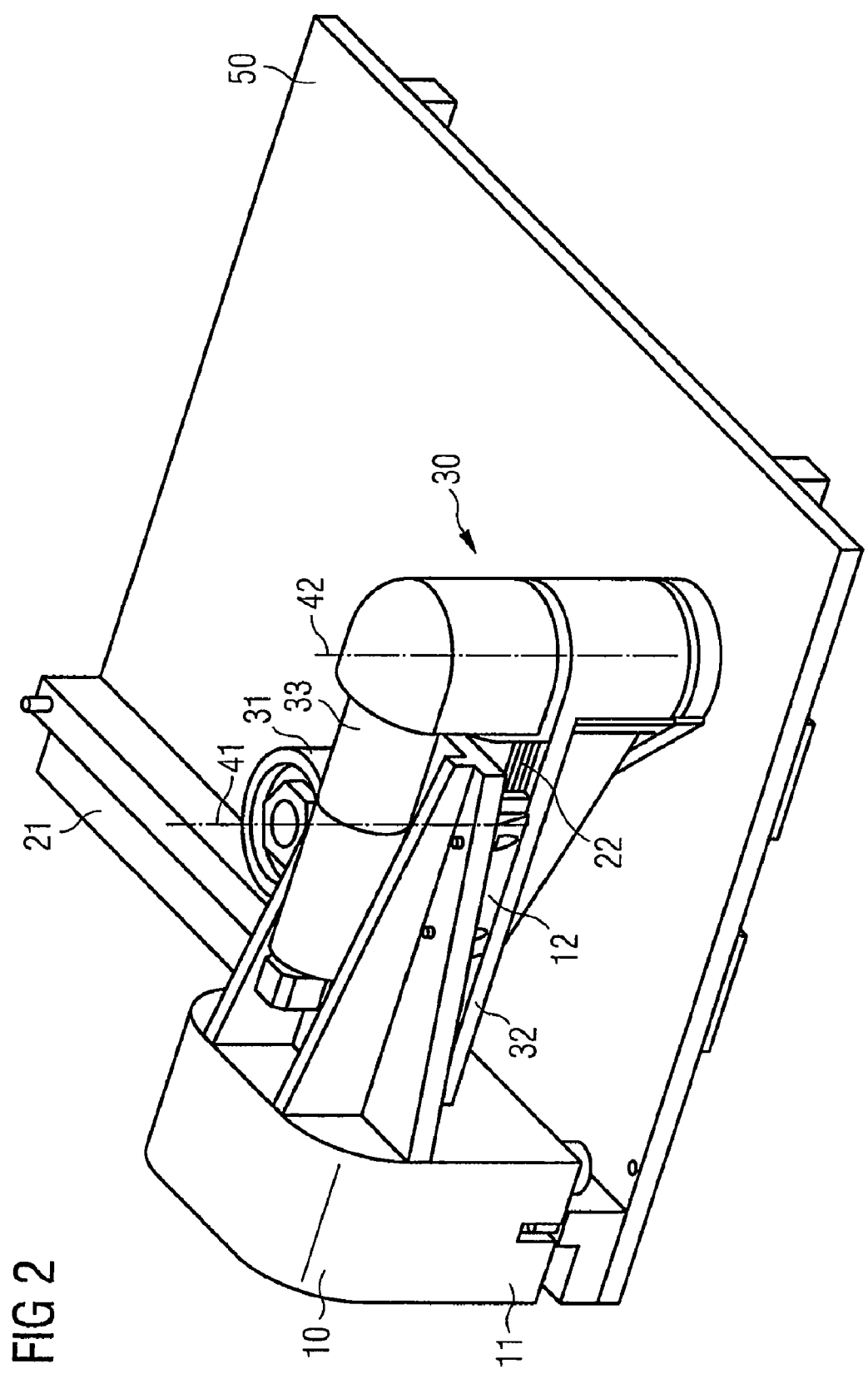
FIG. 2 illustrates a perspective view of one embodiment of a movement system with a double motion link.
Figure 3:
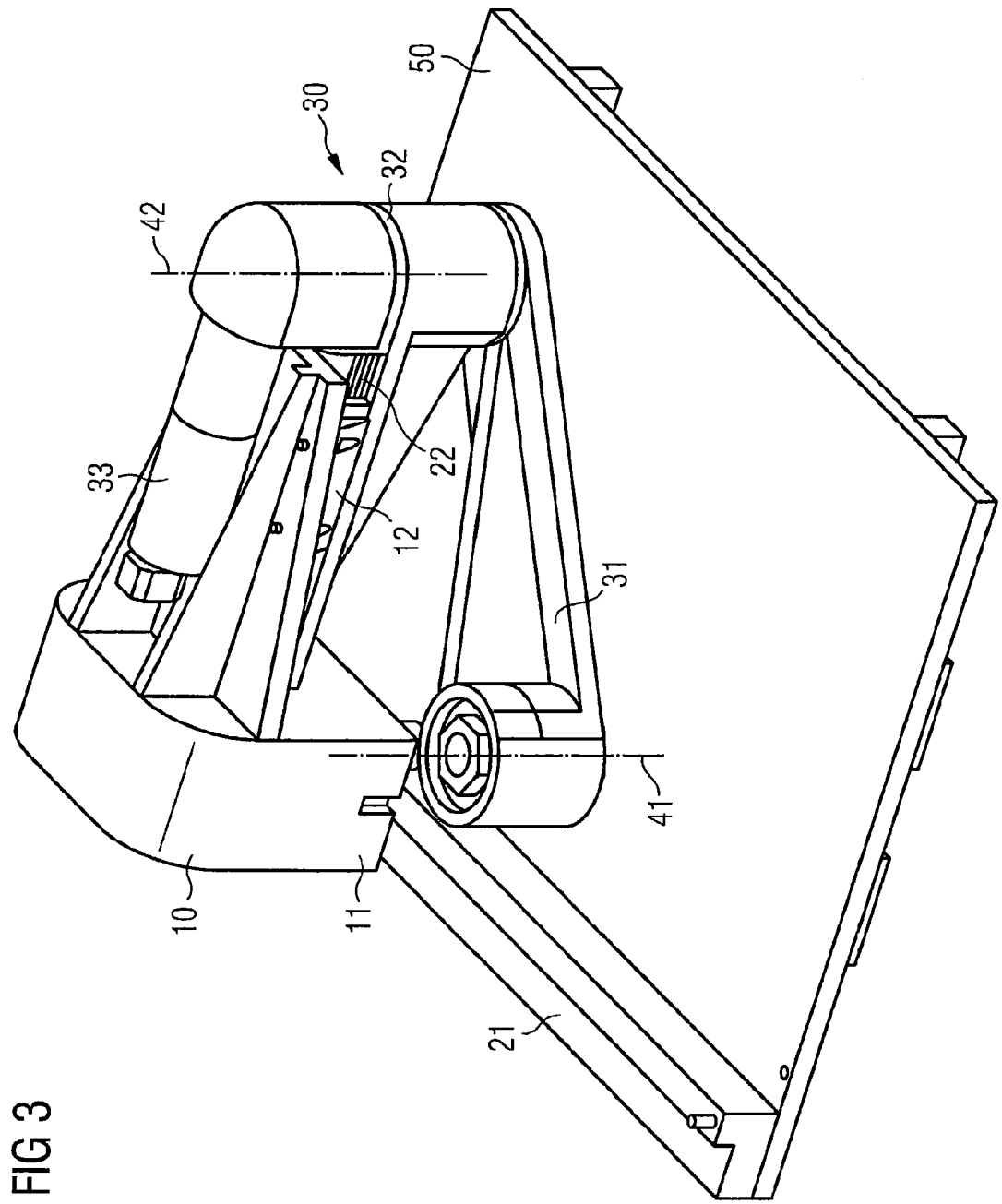
FIG. 3 illustrates a further perspective view of the movement system with a double motion link.
Figure 4:
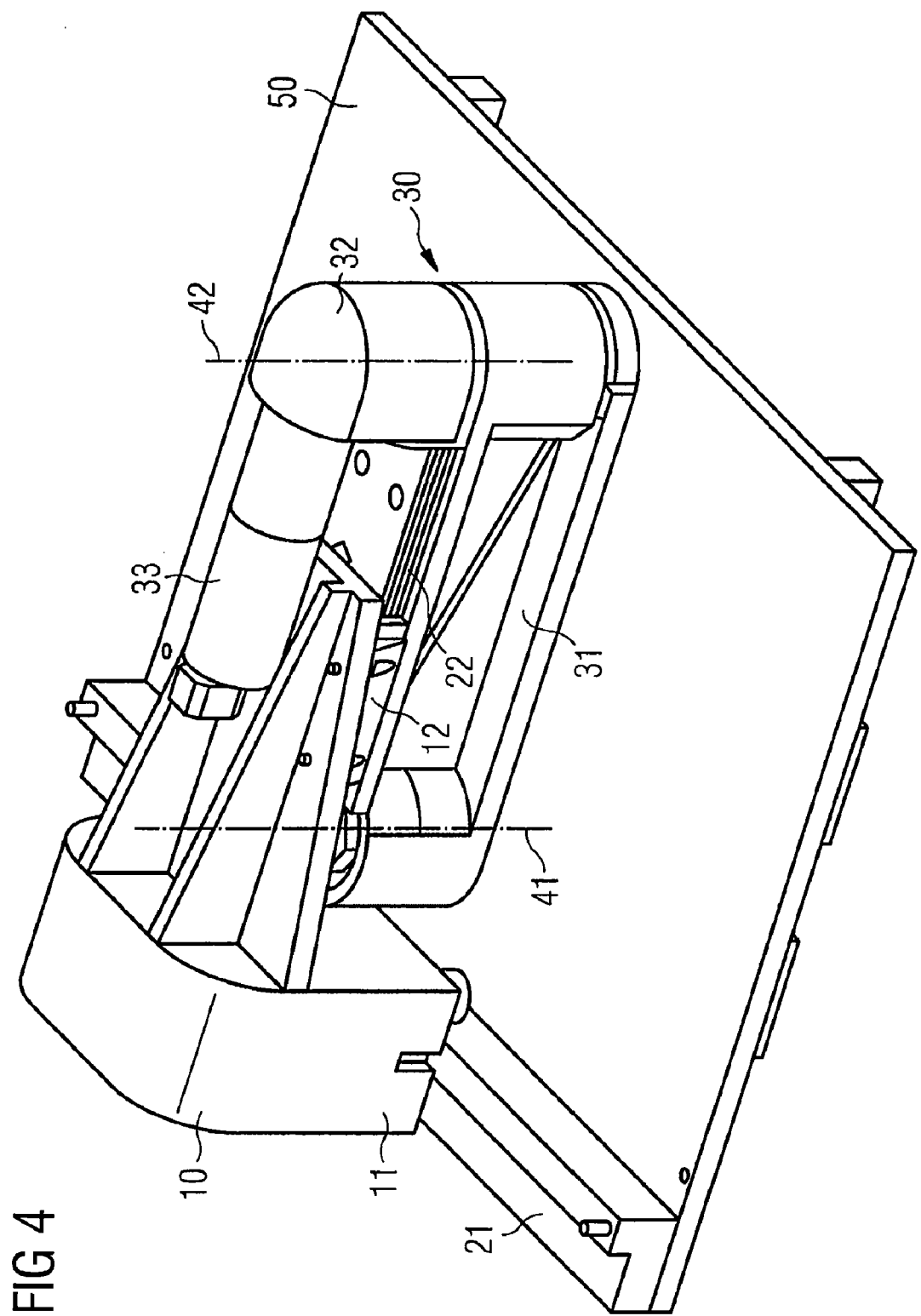
FIG. 4 illustrates a further perspective view of a movement system with a double motion link and FIG. 5 illustrates an overhead view of a movement system with a double motion link.

FIGS. 2, 3 and 4 show perspective views of a movement system in different movement positions. Arranged on a carrier plate 50 is a first guide element 21 on which a movement device 10 with a first carriage 11 is supported to allow movement. Mounted on a rotatable support around the first axis of rotation 41 is the first motion link 31 of a double motion link 30. The first axis of rotation 41 is at right angles to the carrier plate 50. A second motion link 32 or the double motion link 30 is connected rotatably to the first motion link 31 around a second axis of rotation 42. The second axis of rotation 42 is at right angles to the carrier plate 50. A second motion link 32 is located above the first motion link 31. Arranged on the second motion link is the second guide element 22. The second guide element 22 may be arranged in parallel to the carrier plate 50 as well as at right angles to the first guide element 21. A second carriage 12 may be connected to the movement device 10. The second carriage 12 may move the movement device 10 on the second motion link 32.

A drive device 33 may be a connecting element between the movement device 10 and a second motion link 32. The drive device 33 may move the movement device 10 along the second guide element 22. The second axis of rotation 42 performs a circular movement around the first axis of rotation 41 and the movement device 10 is moved in parallel to the carrier plate 50 on the first guide element. Together with the second guide element 22, the second carriage 12 may form a length compensation for a movement of the movement device 10 along the first guide element 21.

FIG. 2 shows the movement device 10 situated in a first end position. The motion links 31, 32 of the double motion link 30 form a maximum opening angle in the second axis of rotation 42.

FIG. 3 shows the movement device 10 having been moved in a second end position symmetrical to a central location. The motion links 31, 32 of the double motion link 30 again form a maximum angle of opening, this time in the opposite direction.

FIG. 4 shows the movement device 10 in the central position. The two motion links 31, 32 of the double motion link 30 cover each other. The opening angle is zero. The second axis of rotation 42 is located in this position at its greatest distance from the first guide element 21.

Figure 5:
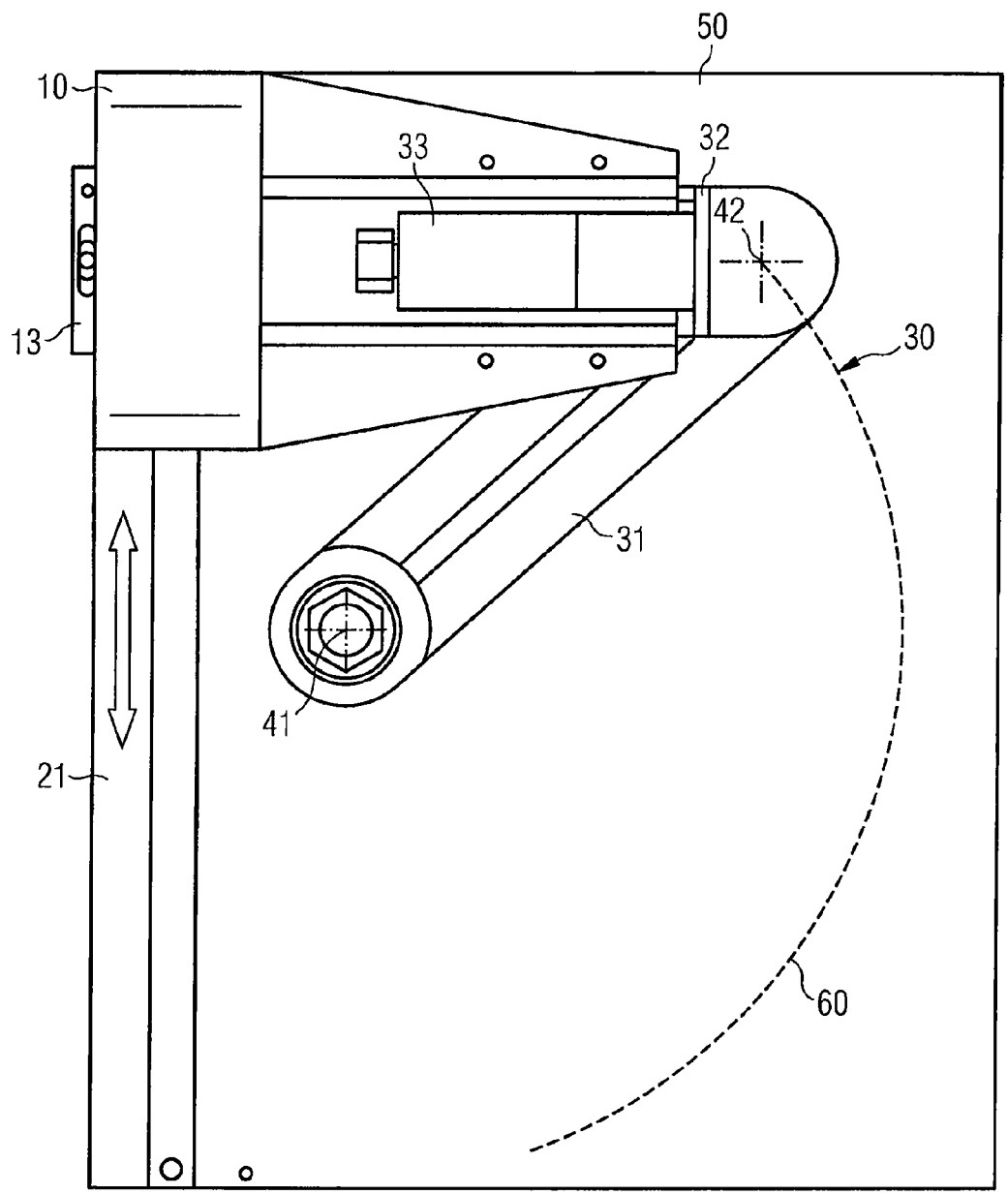

FIG. 5 shows an overhead view of the movement system with a double motion link 30. Arranged on a carrier plate 50 is a first guide element 21, for example, a rail system. Supported movably on the first guide element 21 is a movement device 10. The double motion link 30 may include a first and second motion link 31, 32 connected in a common second axis of rotation 42. The double motion link 30 may connect the movement device 10 to the carrier plate around a first axis of rotation standing at right angles to the carrier plate 50. The drive device 33 may move the movement device 10 along the second motion link 32 of the double motion link 30. This causes the second axis of rotation 42 to move along a circular path 60 around the first axis of rotation 41. By this rotational movement along the circular path 60, the movement device 10 is moved along the first guide element 21. The double motion link 30 offers the length compensation for this parallel movement. A C-arm may be mounted on the movement device 10 via a coupling element 13. With a suitable arrangement in an x-ray facility the C-arm may be moved in parallel to a patient bed, for example.

Leverages which are transmitted via decoupling element 13 to the movement device 10 can be transmitted in this way equally to the first guide element 21 and via the double motion link 30 and the first axis of rotation 41 to the carrier plate 50. As a result, there is no jamming of the movement device 10 when it is moved along the first guide element 21.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A movement system for a c-arm arranged on a trolley, the movement system comprising:
   at least one first guide element arranged in a plane,
   a movement device arranged movably along the at least one first guide element, a first motion link that is rotatable around a first axis of rotation at right angles to the plane, the movement device and the first motion link being connected to a second axis of rotation standing at right angles to the plane such that a movement of the movement device along the at least one first guide element causes the second axis of rotation to move on a circular track around the first axis of rotation,
   a second motion link forming the rotatable connection between the movement device and the first motion link, and
   at least one second guide element arranged on the second motion link in parallel to the plane and at right angles to the at least one first guide element, the movement device being moveable along the at least one second guide element.

2. The movement system as claimed in claim 1, wherein the plane is aligned horizontally.

3. The movement system as claimed in claim 1, wherein the first motion link and the second motion link form a double motion link, the second motion link being arranged above the first motion link.

4. The movement system as claimed in claim 1, wherein a drive device is connected to the movement device and is arranged on the second motion link such that when the movement device is moved along the at least one second guide element, the movement device is moved along the at least one first guide device.

5. The movement system as claimed in claim 1, wherein a leverage acting on the movement device is partly introducible via the first motion link into the first axis of rotation.

6. The movement system as claimed in claim 1, wherein the movement device comprises a first carriage moveable in or on the at least one first guide element and a second carriage moveable in or on the at least one second guide element.

7. The movement system as claimed in claim 1, wherein the at least one first guide element comprises a first rail system, and the at least one second guide element comprises a second rail system.

8. The movement system as claimed in claim 1, wherein the movement device is moveable approximately +/−200 mm around a central position.

9. A C-arm comprising:
an x-ray emitter operable to emit x-radiation,
an x-ray detector operable to detect the x-rays emitted from the x-ray emitter, and
a movement system comprising:
  at least one first guide element arranged in a plane,
  a movement device arranged movably along the at least one first guide element,
  a first motion link that is rotatable around a first axis of rotation at right angles to the plane, the movement device and the first motion link being connected to a second axis of rotation standing at right angles to the plane such that a movement of the movement device along the at least one first guide element causes the second axis of rotation to move on a circular track around the first axis of rotation,
  a second motion link forming the rotatable connection between the movement device and the first motion link, and
  at least one second guide element arranged on the second motion link in parallel to the plane and at right angles to the at least one first guide element, the movement device being moveable along the at least one second guide element,
wherein the C-arm is arranged on the movement device such that the C-arm is moveable in parallel to a patient bed.

10. An x-ray movement device comprising:
a C-arm comprising:
  an x-ray emitter operable to emit x-radiation,
  an x-ray detector o erable to detect the x-rays emitted from the x-ray emitter, and
  a movement system comprising:
    at least one first guide element arranged in a plane,
    a movement device arranged movably along the at least one first guide element,
    a first motion link that is rotatable around a first axis of rotation at right angles to the plane, the movement device and the first motion link being connected to a second axis of rotation standing at right angles to the plane such that a movement of the movement device along the at least one first guide element causes the second axis of rotation to move on a circular track around the first axis of rotation,
    a second motion link forming the rotatable connection between the movement device and the first motion link, and
    at least one second guide element arranged on the second motion link in parallel to the plane and at right angles to the at least one first guide element, the movement device being moveable along the at least one second guide element,
wherein the C-arm is arranged on the movement device such that the C-arm is moveable in parallel to a patient bed.

* * * * *